US00PP26882P3

(12) United States Plant Patent
Puterbaugh

(10) Patent No.: US PP26,882 P3
(45) Date of Patent: Jun. 28, 2016

(54) HOP PLANT NAMED 'LD1817'

(50) Latin Name: *Humulus lupulus*
Varietal Denomination: LD1817

(71) Applicant: Puterbaugh Farms Partnership, Mabton, WA (US)

(72) Inventor: Stacey Martin Puterbaugh, Mabton, WA (US)

(73) Assignee: Puterbaugh Farms Partnership, Mabton, WA (US)

( * ) Notice: Subject to any disclaimer, the term of this patent is extended or adjusted under 35 U.S.C. 154(b) by 233 days.

(21) Appl. No.: 13/998,106

(22) Filed: Oct. 1, 2013

(65) Prior Publication Data

US 2014/0096297 P1 Apr. 3, 2014

Related U.S. Application Data

(60) Provisional application No. 61/744,835, filed on Oct. 3, 2012.

(51) Int. Cl.
*A01H 5/02* (2006.01)

(52) U.S. Cl.
USPC ..... Plt./236
CPC ..... *A01H 5/02* (2013.01)

(58) Field of Classification Search
USPC ..... Plt./236
CPC ..... A01H 5/00
See application file for complete search history.

*Primary Examiner* — Kent L Bell
(74) *Attorney, Agent, or Firm* — Michelle Bos

(57) ABSTRACT

'LD1817' is a strong, hearty hop plant, dark green in color with relatively large leaves in comparison to other hops. 'LD1817' easily reaches the full 18-foot height of the hop trellis with heavy vines and foliage. The cones, once fully matured, measure about 3 cm to 5 cm inches in length, are abundant on the vine, and have a pleasing, fruity aroma with moderate alpha acids.

6 Drawing Sheets

Latin name: *Humulus lupulus.*
Variety denomination: 'LD1817'.

BACKGROUND OF THE VARIETY

'LD1817' is a new and distinct variety of hop plant (*Humulus lupulus*). This new variety was discovered in 2009 as a chance seedling near an existing hop field near Mabton, Wash. The parentage of the new variety is unknown, although it is believed that 'Magnum' may be a parent. 'LD1817' was asexually reproduced by cutting the same year near Mabton, Wash., and was planted in the field in 2010 and 2011. 'LD1817' has been observed to remain true to type over successive asexually propagated generations.

BRIEF DESCRIPTION OF THE VARIETY

The 'LD1817' hop plant is distinguished from other known hop plants by its large leaves, vigorous growth habit, and aromatic cones. 'LD1817' is a strong, hearty plant, dark green in color with abnormally large leaves (in comparison to other hops). 'LD1817' easily reaches the full 18-foot height of the hop trellis with heavy vines and foliage. The cones, once fully matured, measure about 3 cm to 5 cm inches in length, are abundant on the vine, and have a pleasing, fruity aroma with moderate alpha acids. Picking dates for the 'LD1817' hop are usually late September, around September 15 to 25. The 'LD1817' hop plant yields about 1600 to 1800 pounds of hop cones per acre.

Genotyping analysis shows that the 'LD1817' variety is most closely related to unpatented varieties 'Kitomadora' and 'Magnum', although these varieties are not grown in or near the location where the seedling was found. A comparison of 'LD1817' and 'Magnum' is shown in the following table:

| Characteristic | 'Magnum' | 'LD1817' |
|---|---|---|
| Aroma profile | No distinct characteristics; primarily used for bittering | Strong orange, slight grapefruit, tropical pineapple, strawberry, melon |
| Maturity | Late-season | Early- to mid-season |
| Alpha acids | 11.0 to 16.0% | 10.0 to 11.0% |
| Beta acids | 5.0 to 7.0% | 4.0 to 5.0% |
| Storage stability | Very good | Good |
| Cone size | Very large, heavy cones throughout plant | Moderate size, abundant in upper canopy |

BRIEF DESCRIPTION OF THE PHOTOGRAPHS

Figure 1:
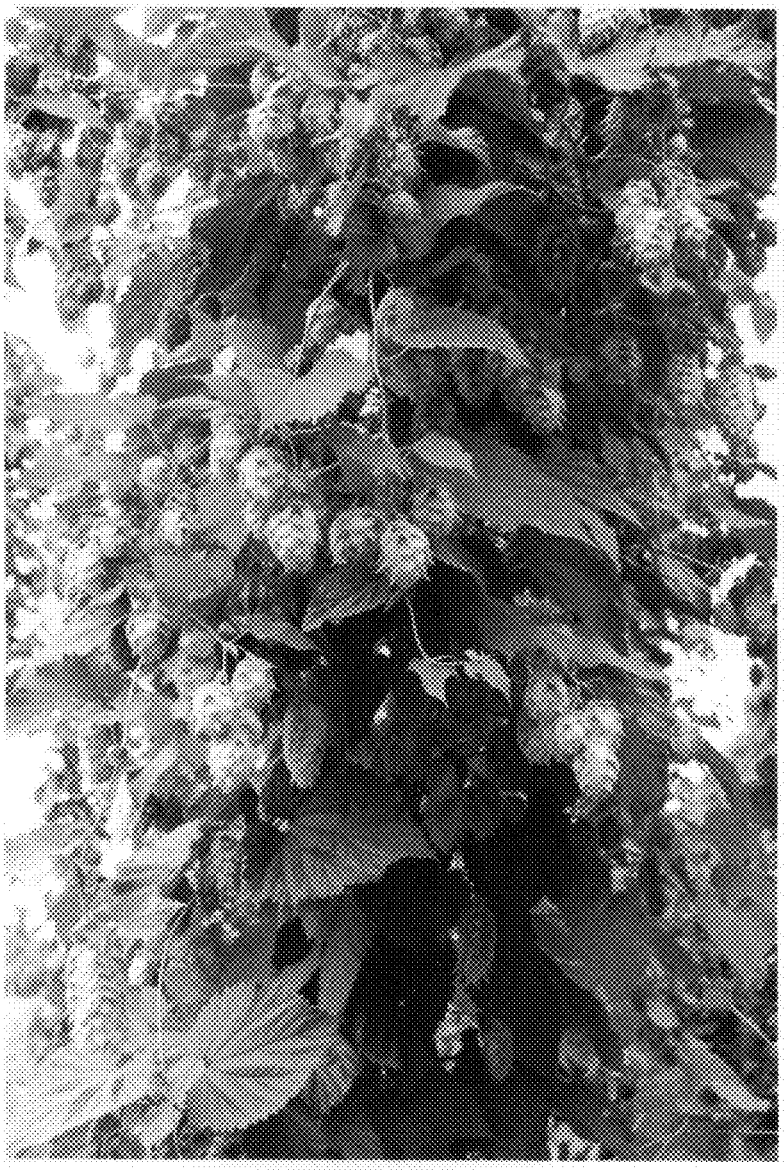
Figure 2:
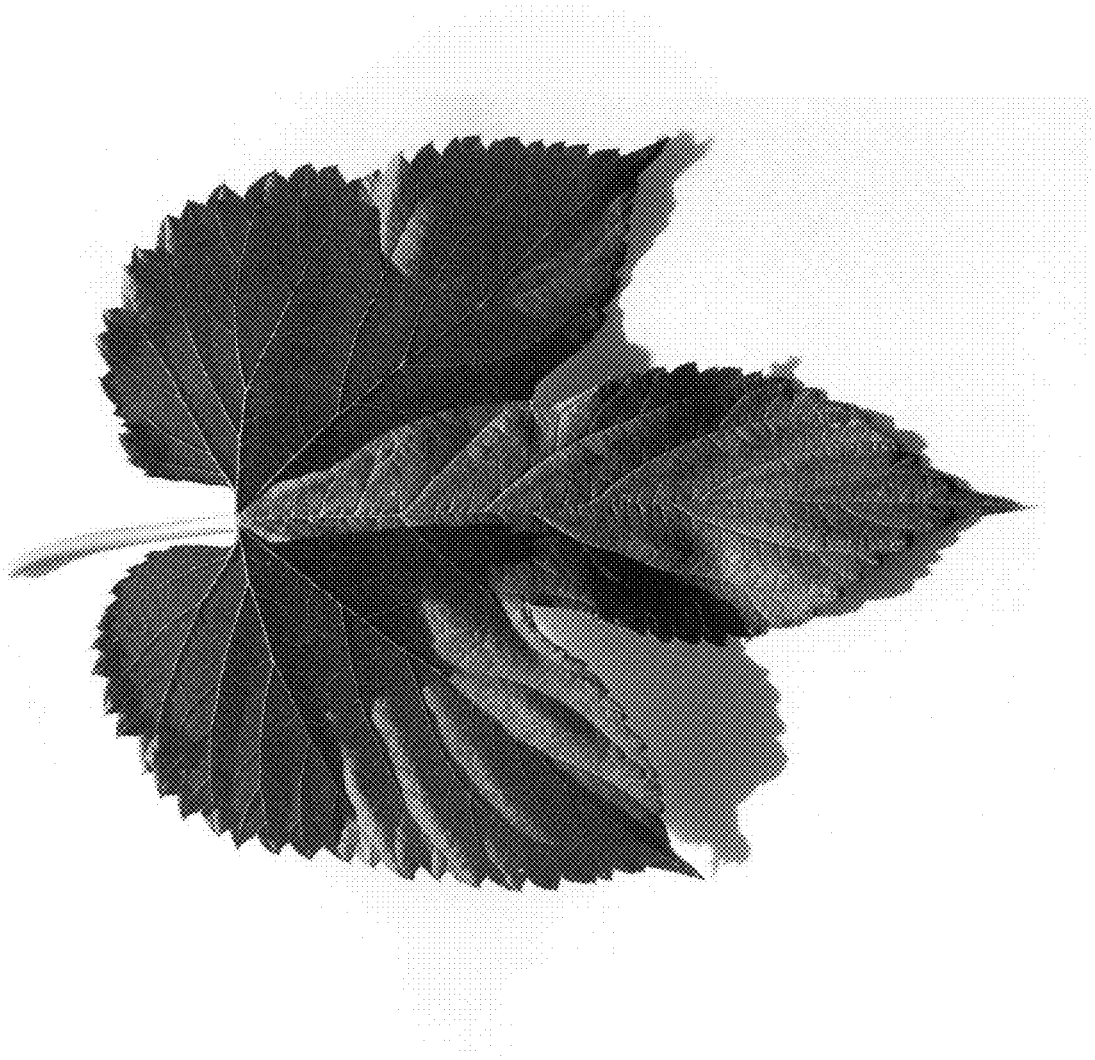
Figure 3:
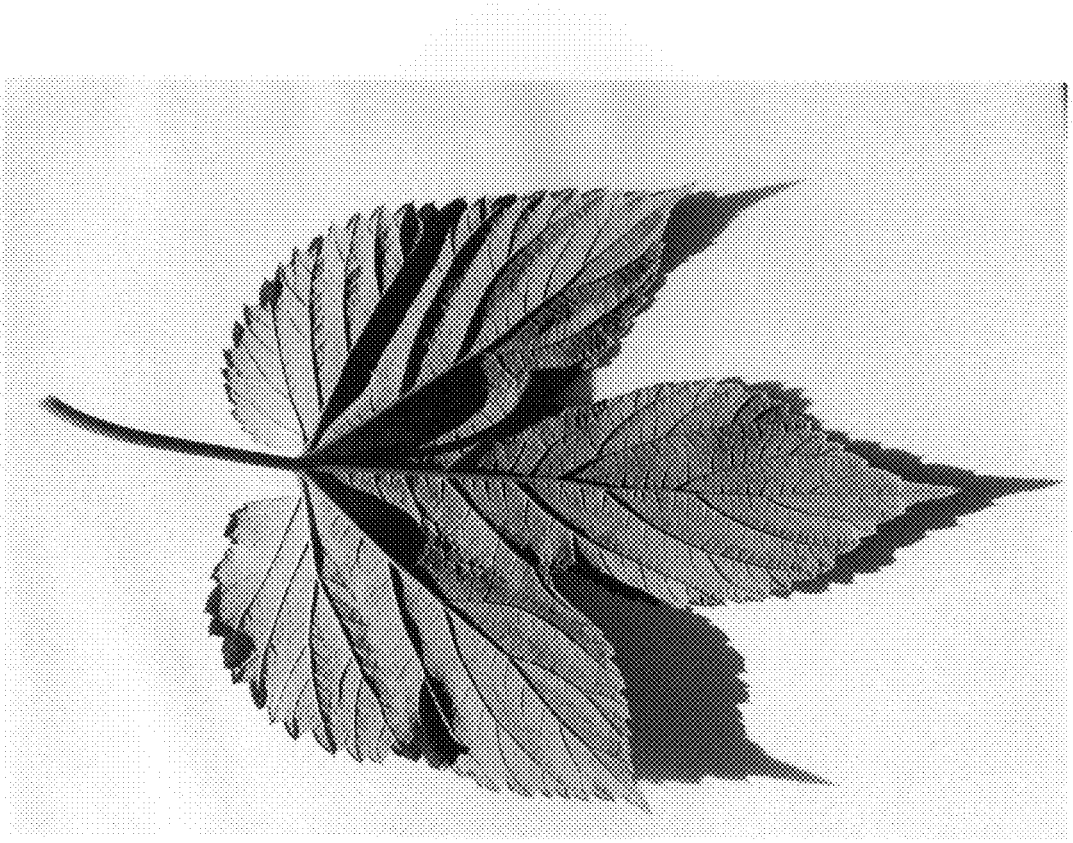
Figure 4:
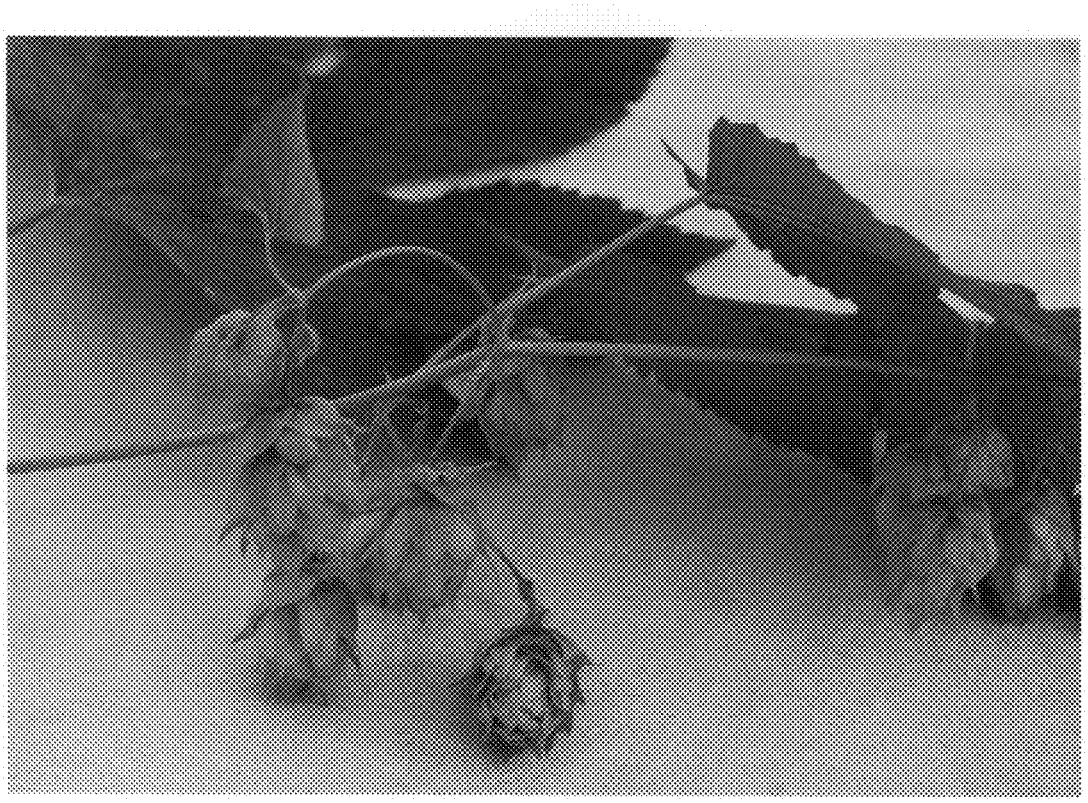
Figure 5:
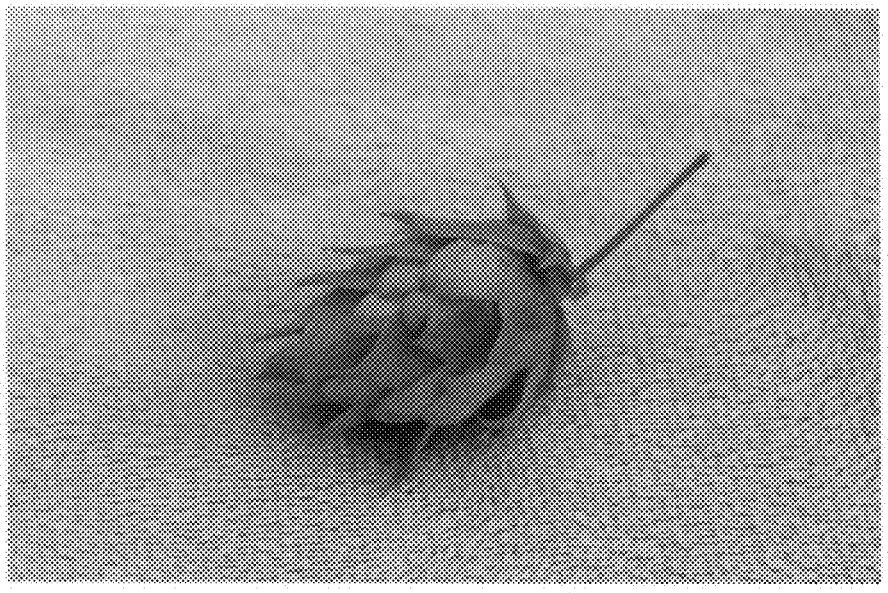
Figure 6:
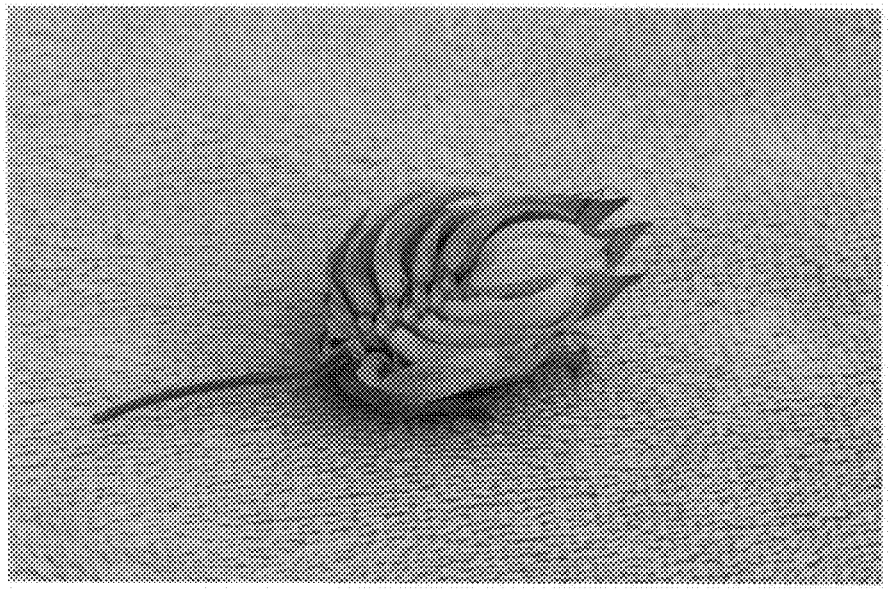
Figure 7:
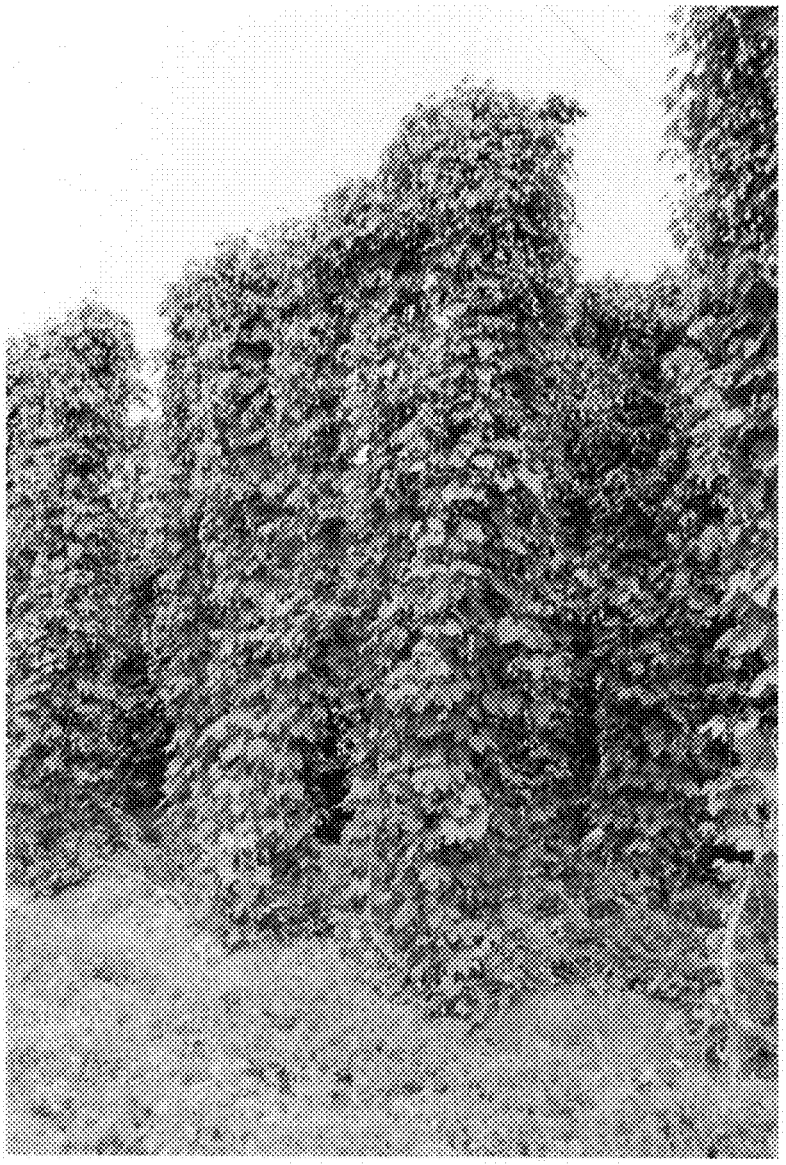

FIG. 1 shows the leaves and cones of the 'LD1817' hop plant;
FIG. 2 shows the upper surface of a leaf of the 'LD1817' hop plant;
FIG. 3 shows the lower surface of a leaf of the 'LD1817' hop plant;
FIG. 4 shows the cones of the 'LD1817' hop plant;
FIG. 5 shows a cone of the 'LD1817' hop plant;
FIG. 6 shows a cone of the 'LD1817' hop plant; and
FIG. 7 shows 'LD1817' hop plants growing on a conventional hop trellis.

BOTANICAL DESCRIPTION OF THE VARIETY

The botanical description herein is based on observations made of 'LD1817' hop plants growing at Mabton, Wash.

during August and September 2013. All colors are described according to The Royal Horticultural Society Colour Chart (2007). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Plant:

*Shape*.—Cylindrical.
*Bine color*.—Yellow-green 144B, 145A.
*Bine stripe*.—Absent or very faint.
*Stipule color*.—Yellow-green 144B.
*Stipule direction*.—Upward.
*Bine diameter*.—8 mm.
*Internode distance*.—17 cm.
*Shoot emergence*.—Early spring (March-April).

Leaves:

*Leaf arrangement*.—Opposite.
*Leaf shape*.—Palmate.
*Number of lobes*.—3 to 5.
*Apex*.—Acuminate.
*Base*.—Auriculate.
*Margin*.—Serrate.
*Serrations per inch*.—4 to 5.
*Pose*.—Horizontal.
*Average length*.—15 cm.
*Average width*.—15 cm.
*Color of mature leaf, upper surface*.—Yellow-green 147A.
*Color of mature leaf, lower surface*.—Yellow-green 147B.
*Color of immature leaf, upper surface*.—Yellow-green 146A.
*Color of immature leaf, lower surface*.—Yellow-green 147B.
*Petiole length*.—9 cm.
*Petiole diameter*.—5 mm.
*Venation*.—Palmate.
*Vein color*.—Yellow-green 146B.

Laterals:

*Length* (*at* 150 *cm*).—34 cm.
*Diameter*.—3 mm.
*Color*.—Yellow-green 146C.
*Internode length*.—16 cm.
*Stipule position*.—Outward.
*Stipule color*.—Yellow-green 146C.

Cones (as measured Sep. 6, 2013):

*Length*.—32 mm.
*Diameter*.—24 mm.
*Number of cones per basal lateral node*.—24 mm.
*Cone shape*.—Broad ovate.
*Compactness*.—Moderate to loose.
*Weight*.—2 g.
*Bract color* (*outer surface*).—Yellow-green 146D.
*Bract color* (*inner surface*).—Yellow-green 145A, 145B.
*Bract shape*.—Cordate to lanceolate.
*Bract tip shape*.—Acuminate.
*Bract tip position*.—Flat to everted.
*Bract length*.—1.5 cm to 2 cm.
*Bract width*.—1 cm.
*Bracteole shape*.—Cordate to lanceolate.
*Bracteole tip shape*.—Acuminate.
*Bracteole tip position*.—Flat to everted.
*Bracteole length*.—1.5 cm to 2 cm.
*Bracteole width*.—1 cm.
*Strig size*.—1.8 cm long, 3 mm diameter.
*Lupulin glands* (*relative quantity*).—Moderate.
*Lupulin gland shape*.—Imperfect sphere.
*Aroma*.—Mild; notes of orange, grapefruit, pineapple, strawberry, melon.

Analytical data:

*Alpha acids*.—10.0% to 11.0%.
*Beta acids*.—4.0% to 5.0%.
*Cohumulone*.—17% to 27%.
*Total oil*.—0.8%.
*Myrcene*.—65% to 67%.
*Humulene*.—13% to 14%.
*Caryophyllene*.—1% to 2%.
*Farnesene*.—<1%.

Yield per acre: 1600 to 1800 lbs/acre.
Harvest maturity: Mid to late Sep. 30, 2013.
Powdery mildew resistance: Good.

I claim:

1. A new and distinct hop plant substantially as described and illustrated herein.

* * * * *